US010648005B2

(12) United States Patent
Woo et al.

(10) Patent No.: US 10,648,005 B2
(45) Date of Patent: May 12, 2020

(54) TRANSFORMED *SYNECHOCOCCUS ELONGATUS* STRAINS HAVING IMPROVED PRODUCTIVITY OF FARNESENE AND USE THEREOF

(71) Applicant: RESEARCH & BUSINESS FOUNDATION SUNGKYUNKWAN UNIVERSITY, Suwon-Si, Gyeonggi-Do (KR)

(72) Inventors: Han-Min Woo, Yongin-si (KR); Hyun-Jeong Lee, Gwangmyeong-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 45 days.

(21) Appl. No.: 16/149,750

(22) Filed: Oct. 2, 2018

(65) Prior Publication Data
US 2019/0119703 A1    Apr. 25, 2019

(30) Foreign Application Priority Data
Oct. 23, 2017   (KR) .................. 10-2017-0137227

(51) Int. Cl.
*C12N 1/20* (2006.01)
*C12P 5/00* (2006.01)
(Continued)

(52) U.S. Cl.
CPC ............... *C12P 5/007* (2013.01); *C12N 1/20* (2013.01); *C12N 9/1022* (2013.01);
(Continued)

(58) Field of Classification Search
None
See application file for complete search history.

(56) References Cited

U.S. PATENT DOCUMENTS

2019/0119703 A1 * 4/2019 Woo .................. C12P 5/007

FOREIGN PATENT DOCUMENTS

KR    10-2009-0013814 A    2/2009

OTHER PUBLICATIONS

Choi et al., "Photosynthetic conversion of CO2 to farnesyl diphosphate-derived phytochemicals (amorpha-4,11-diene and squalene) by engineered cyanobacteria",Biotechnology for Biofuels, 2016, vol. 9:202, pp. 1-12.

(Continued)

*Primary Examiner* — Richard C Ekstrom
(74) *Attorney, Agent, or Firm* — NSIP Law

(57) ABSTRACT

The present disclosure relates to the transformed Synechococcus elongatus strain of capable of mass production of farnesene. The transformed Synechococcus elongatus strain of the present disclosure is characterized by having the ability to mass produce farnesene using carbon dioxide as an independent carbon source. In particular, the Synechococcus elongatus strain is economically effective because it uses carbon dioxide present in light and air as a carbon source. There is an eco-friendly effect since it can be used for eliminating or reducing carbon dioxide in the atmosphere using microorganisms. Further, the strain of the present disclosure has a rapid growth rate and excellent ability to fix carbon dioxide compared with other microorganisms, thereby being utilized in various fields such as food, medicine, pharmacy, biofuel, and chemistry.

15 Claims, 7 Drawing Sheets

Specification includes a Sequence Listing.

(51) Int. Cl.
  *C12P 23/00*   (2006.01)
  *C12N 15/62*   (2006.01)
  *C12N 9/12*    (2006.01)
  *C12N 9/10*    (2006.01)
  *C12R 1/01*    (2006.01)
  *C12N 9/90*    (2006.01)
  *C12N 9/16*    (2006.01)
  *C12N 15/52*   (2006.01)
  *C12N 9/88*    (2006.01)

(52) U.S. Cl.
  CPC .............. *C12N 9/1205* (2013.01); *C12N 9/16* (2013.01); *C12N 9/88* (2013.01); *C12N 9/90* (2013.01); *C12N 15/52* (2013.01); *C12N 15/62* (2013.01); *C12P 23/00* (2013.01); *C12R 1/01* (2013.01); *C12Y 202/01007* (2013.01); *C12Y 301/07011* (2015.07); *C12Y 503/03002* (2013.01)

(56) References Cited

OTHER PUBLICATIONS

Chwa et al., "Engineering of a modular and synthetic phosphoketolase pathway for photosynthetic production of acetone from CO2 in Synechococcus elongatus PCC 7942 under light and aerobic condition", Plant Biotechnology Journal, 2016, vol. 14, pp. 1768-1776.

Kim et al., "Development of SyneBrick Vectors As a Synthetic Biology Platform for Gene Expression in Synechococcus elongatus PCC 7942", Frontiers in Plant Science, 2017, vol. 8, Article 293, pp. 1-9.

\* cited by examiner

NSI : OverMEP (G3P + PYR → FPP)

NSII : FS (FPP → Farnesene)

SEQUENCE LISTING

```
<160> NUMBER OF SEQ ID NOS: 8

<210> SEQ ID NO 1
<211> LENGTH: 1863
<212> TYPE: DNA
<213> ORGANISM: Artificial Sequence
<220> FEATURE:
<223> OTHER INFORMATION: dxs DNA sequence

<400> SEQUENCE: 1
atgagctttg atatcgccaa ataccccacc ctggccctgg tggatagcac ccaggaactg      60
cgcctgctgc ccaaagaaag cctgcccaaa ctgtgcgatg aactgcgccg ctacctgctg     120
gatagcgtga gccgcagcag cggccacttt gccagcggcc tgggcaccgt ggaactgacc     180
gtggccctgc actacgtgta caacaccccc tttgatcagc tgatctggga tgtgggccac     240
caggcctacc cccacaaaat cctgaccggc cgccgcgata aaatcggcac catccgccag     300
aaaggcggcc tgcacccctt tccctggcgc ggcgaaagcg aatacgatgt gctgagcgtg     360
ggccacagca gcaccagcat cagcgccggc atcggcatcg ccgtggccgc cgaaaaagaa     420
ggcaaaaacc gccgcaccgt gtgcgtgatc ggcgatggcg ccatcaccgc cggcatggcc     480
tttgaagcca tgaaccacgc cggcgatatc cgccccgata tgctggtgat cctgaacgat     540
aacgaaatga gcatcagcga aaacgtgggc gccctgaaca accacctggc ccagctgctg     600
agcggcaaac tgtacagcag cctgcgcgaa ggcggcaaaa aagtgtttag cggcgtgccc     660
cccatcaaag aactgctgaa acgcaccgaa gaacacatca aaggcatggt ggtgcccggc     720
accctgtttg aagaactggg ctttaactac atcggccccg tggatggcca cgatgtgctg     780
ggcctgatca ccaccctgaa aaacatgcgc gatctgaaag gcccccagtt cctgcatatc     840
atgaccaaaa aaggccgcgg ctacgaaccc gccgaaaaag atcccatcac ctttcacgcc     900
gtgcccaaat tgatcccag cagcggctgc ctgcccaaaa gcagcggcgg cctgcccagc     960
tacagcaaaa tctttggcga ttggctgtgc gaaaccgccg ccaaagataa caaactgatg    1020
```

| | |
|---|---|
| gccatcacccc cgccatgcg cgaaggcagc ggcatggtgg aatttagccg caaatttccc | 1080 |
| gatcgctact tgatgtggc catcgccgaa cagcacgccg tgacctttgc cgccggcctg | 1140 |
| gccatcggcg gctacaaacc catcgtggcc atctacagca cctttctgca gcgcgcctac | 1200 |
| gatcaggtgc tgcacgatgt ggccatccag aaactgcccg tgctgtttgc catcgatcgc | 1260 |
| gccggcatcg tgggcgccga tgccagacc caccagggcg cctttgatct gagctacctg | 1320 |
| cgctgcatcc ccgaaatggt gatcatgacc cccagcgatg aaaacgaatg ccgccagatg | 1380 |
| ctgtacaccg gctaccacta caacgatggc cccagcgccg tgcgctaccc ccgcggcaac | 1440 |
| gccgtgggcg tggaactgac cccctggaa aaactgccca tcggcaaagg catcgtgaaa | 1500 |
| cgccgcggcg aaaaactggc catcctgaac tttggcaccc tgatgcccga agccgccaaa | 1560 |
| gtggccgaaa gcctgaacgc cacccctggtg gatatgcgct tgtgaaacc cctggatgaa | 1620 |
| gccctgatcc tggaaatggc cgccagccac gaagccctgg tgaccgtgga agaaaacgcc | 1680 |
| atcatgggcg cgccggcag cggcgtgaac gaagtgctga tggccaccg caaacccgtg | 1740 |
| cccgtgctga acatcggcct gccgatttt tttatcccc agggcaccca ggaagaaatg | 1800 |
| cgcgccgaac tgggcctgga tgccgccggc atggaagcca aaatcaaagc ctggctggcc | 1860 |
| tag | 1863 |

<210> SEQ ID NO 2
<211> LENGTH: 549
<212> TYPE: DNA
<213> ORGANISM: Artificial Sequence
<220> FEATURE:
<223> OTHER INFORMATION: idi DNA sequence

<400> SEQUENCE: 2

| | |
|---|---|
| atgcagaccg aacacgtgat cctgctgaac gcccagggcg tgcccaccgg caccctggaa | 60 |
| aaatacgccg cccacaccgc cgatacccgc ctgcacctgg cctttagcag ctggctgttt | 120 |
| aacgccaaag gccagctgct ggtgacccgc gcgccctga gcaaaaaagc ctggcccggc | 180 |
| gtgtggacca acagcgtgtg cggccacccc cagctgggcg aaagcaacga agatgccgtg | 240 |
| atccgccgct gccgctacga actgggcgtg gaaatcaccc ccccgaaag catctacccc | 300 |
| gattttcgct accgcgccac cgatcccagc ggcatcgtgg aaaacgaagt gtgccccgtg | 360 |
| tttgccgccc gcaccaccag cgccctgcag atcaacgatg atgaagtgat ggattaccag | 420 |
| tggtgcgatc tggccgatgt gctgcacggc atcgatgcca cccctgggc ctttagcccc | 480 |
| tggatggtga tgcaggccac caaccgcgaa gcccgcaaac gcctgagcgc ctttacccag | 540 |
| ctgaaatag | 549 |

<210> SEQ ID NO 3
<211> LENGTH: 900
<212> TYPE: DNA
<213> ORGANISM: Artificial Sequence
<220> FEATURE:
<223> OTHER INFORMATION: ispA DNA sequence

<400> SEQUENCE: 3

| | |
|---|---|
| atggatttc cccagcagct ggaagcctgc gtgaaacagg ccaaccaggc cctgagccgc | 60 |
| tttatcgccc ccctgccctt tcagaacacc cccgtggtgg aaaccatgca gtacggcgcc | 120 |
| ctgctgggcg gcaaacgcct gcgcccctt ctggtgtacg ccaccggcca catgtttggc | 180 |
| gtgagcacca cacccctgga tgccccgcc gcgccgtgg aatgcatcca cgcctacagc | 240 |
| ctgatccacg atgatctgcc cgccatggat gatgatgatc tgcgccgcgg cctgcccacc | 300 |

```
tgccacgtga aatttggcga agccaacgcc atcctggccg gcgatgccct gcagaccctg      360
gcctttagca tcctgagcga tgccgatatg cccgaagtga gcgatcgcga tcgcatcagc      420
atgatcagcg aactggccag cgccagcggc atcgccggca tgtgcggcgg ccaggccctg      480
gatctggatg ccgaaggcaa acacgtgccc ctggatgccc tggaacgcat ccaccgccac      540
aaaaccggcg ccctgatccg cgccgccgtg cgcctgggcg ccctgagcgc ggcgataaa       600 ggccgccgcg ccctgcccgt gctggataaa tacgccgaaa gcatcggcct ggcctttcag      660
gtgcaggatg atatcctgga tgtggtgggc gataccgcca ccctgggcaa cgccagggc       720 gccgatcagc agctgggcaa aagcacctac cccgccctgc tgggcctgga acaggcccgc      780
aaaaaagccc gcgatctgat cgatgatgcc cgccagagcc tgaaacagct ggccgaacag      840
agcctggata ccagcgccct ggaagccctg ccgattaca tcatccagcg caacaaatag       900

<210> SEQ ID NO 4
<211> LENGTH: 1731
<212> TYPE: DNA
<213> ORGANISM: Artificial Sequence
<220> FEATURE:
<223> OTHER INFORMATION: AFS DNA sequence

<400> SEQUENCE: 4
atggaatttc gcgtgcacct gcaggccgat aacgaacaga aatctttca gaaccagatg        60 aaacccgaac ccgaagccag ctacctgatc aaccagcgcc gcagcgccaa ctacaaaccc      120
aacatctgga aaacgatttt ctggatcag agcctgatca gcaaatacga tggcgatgaa       180
taccgcaaac tgagcgaaaa actgatcgaa gaagtgaaaa tctacatcag cgccgaaacc      240
atggatctgg tggccaaact ggaactgatc gatagcgtgc gcaaactggg cctggccaac      300
ctgtttgaaa agaaatcaa agaagccctg atagcatcg ccgccatcga aagcgataac       360
ctgggcaccc gcgatgatct gtacggcacc gccctgcact taaaaatcct cgccagcac       420 ggctacaaag tgagccagga tatctttggc cgctttatgg atgaaaaagg caccctggaa      480
aaccaccact tgcccacct gaaaggcatg ctggaactgt ttgaagccag caacctgggc       540
tttgaaggcg aagatatcct ggatgaagcc aaagccagcc tgaccctggc cctgcgcgat      600
agcggccaca tctgctaccc cgatagcaac ctgagccgcg atgtggtgca cagcctggaa      660
ctgcccagcc accgccgcgt gcagtggttt gatgtgaaat ggcagatcaa cgcctacgaa      720
aaagatatct gccgcgtgaa cgccacccctg ctggaactgg ccaaactgaa ctttaacgtg     780
gtgcaggccc agctgcagaa aaacctgcgc gaagccagcc gctggtgggc aaccctgggc      840
atcgccgata acctgaaatt tgcccgcgat cgcctggtgg aatgctttgc ctgcgccgtg      900
ggcgtggcct ttgaacccga acacagcagc tttcgcatct gcctgaccaa agtgatcaac      960
ctggtgctga tcatcgatga tgtgtacgat atctacggca gcgaagaaga actgaaacac     1020
tttaccaacg ccgtggatcg ctgggatagc gcgaaaccg aacagctgcc cgaatgcatg      1080
aaaatgtgct ttcaggtgct gtacaacacc acctgcgaaa tcgcccgcga aatcgaagaa     1140
gaaaacggct ggaaccaggt gctgcccag ctgaccaaag tgtgggccga tttttgcaaa      1200
gccctgctgg tggaagccga atggtacaac aaaagccaca tccccaccct ggaagaatac     1260
ctgcgcaacg gctgcatcag cagcagcgtg agcgtgctgc tggtgcacag ctttttagc       1320 atcacccacg aaggcaccaa agaaatggcc gattttctgc acaaaaacga agatttgctg     1380
tacaacatca gcctgatcgt gcgcctgaac aacgatctgg gcaccagcgc cgccgaacag     1440
```

-continued

```
gaacgcggcg atagcccag cagcatcgtg tgctacatgc gcgaagtgaa cgccagcgaa    1500
gaaaccgccc gcaaaaacat caaaggcatg atcgataacg cctggaaaaa agtgaacggc    1560
aaatgcttta ccaccaacca ggtgcccttt ctgagcagct ttatgaacaa cgccaccaac    1620
atggcccgcg tggcccacag cctgtacaaa gatggcgatg gctttggcga tcaggaaaaa    1680
ggcccccgca cccacatcct gagcctgctg tttcagcccc tggtgaacta g             1731

<210> SEQ ID NO 5
<211> LENGTH: 20
<212> TYPE: DNA
<213> ORGANISM: Artificial Sequence
<220> FEATURE:
<223> OTHER INFORMATION: NSI-foward primer

<400> SEQUENCE: 5
aagcgctccg catggatctg                                                   20

<210> SEQ ID NO 6
<211> LENGTH: 20
<212> TYPE: DNA
<213> ORGANISM: Artificial Sequence
<220> FEATURE:
<223> OTHER INFORMATION: NSI-reverse primer

<400> SEQUENCE: 6
caaggcagct tggaagggcg                                                   20

<210> SEQ ID NO 7
<211> LENGTH: 20
<212> TYPE: DNA
<213> ORGANISM: Artificial Sequence
<220> FEATURE:
<223> OTHER INFORMATION: NSII-forward primer

<400> SEQUENCE: 7
ggctacggtt cgtaatgcca                                                   20

<210> SEQ ID NO 8
<211> LENGTH: 20
<212> TYPE: DNA
<213> ORGANISM: Artificial Sequence
<220> FEATURE:
<223> OTHER INFORMATION: NSII-reverse primer

<400> SEQUENCE: 8
gagatcaggg ctgtacttac                                                   20
```

TRANSFORMED *SYNECHOCOCCUS ELONGATUS* STRAINS HAVING IMPROVED PRODUCTIVITY OF FARNESENE AND USE THEREOF

CROSS-REFERENCE TO RELATED APPLICATIONS

This application claims the benefit of priority from Korean Patent Application No. KR10-2017-0137227, filed on Oct. 23, 2017, the contents of which is incorporated herein by reference.

FIELD OF THE INVENTION

The present disclosure relates to transformed *Synechococcus elongatus* strains capable of mass production of farnesene from carbon dioxide, a method of producing farnesene and a method of reducing or eliminating carbon dioxide using the same.

BACKGROUND OF THE INVENTION

Isoprenoid is a substance that plays a critical role in living organisms, which is used to maintain cell's fluidity, electron transfer and another metabolism. Isoprenoid includes a diverse group consisting of more than 40,000 products, many natural isoprenoids and synthetic isoprenoids of which are used as medicines, cosmetics, perfumes, pigments, coloring agents, fungicides, preservatives, functional foods and fine chemical intermediates.

Further, in a natural state, isoprenoid is synthesized by continuous condensation reaction of isopentenyl diphosphate (IPP), which is a precursor thereof, and dimethylallyl pyrophosphate (DMAPP), which is an isomer thereof. Two routes are known for the precursor. Except for plants, eukaryotes generally use a mevalonate-dependent pathway (MVA) to convert acetyl coenzyme A (acetyl-CoA) to IPP. Here, the IPP later becomes an isomer as DMAPP. Although there are some exceptions, prokaryotes typically use the only mevalonate-independent pathway or the deoxyxylulose-5-phosphate pathway (MEP) to generate IPP and DMAPP. Plants use both of MVA and MEP pathways.

Typically, isoprenoid has been prepared via extraction from natural sources such as plants, microorganisms, and animals. However, yields are usually very low because there are many severe limitations to extraction. First, most isoprenoid accumulates only in small amounts under natural conditions. Second, feed organisms are typically not suitable for mass-scale cultivation processes which are necessary to produce commercially useful amounts of desired isoprenoids. Third, isoprenoid extraction requires any toxic solvent, and particular attention should be paid to the handling and processing of this solvent, so there are many difficulties in the commercial production of isoprenoid.

Moreover, a sesquiterpene, a class of isoprenoid extracted from plants, is known to have important medical and industrial properties (Berger, 2009; Dhingra et al., 2009; Muntendam et al., 2009). Farnesene has recently been developed as biofuel precursors due to hydrogenation reactions of farnesene (Renneger and McPhee, 2008). But, only naturally small amounts thereof are produced. Accordingly, it is expected that metabolic engineering is an alternative pathway for mass production of such rare and valuable compounds from *E. coli* and yeast. It is necessary for developing technology to mass-produce farnesene with a significant industrial value.

SUMMARY OF THE INVENTION

The present inventors have produced transformed Synechococcus elongatus strains capable of mass-producing farnesene through genetic engineering, focusing on Synechococcus elongatus, a type of cyanobacterium which is a prokaryotic cell, produced farnesene using the transformant strain in mass production, and further confirmed that the carbon dioxide could be effectively reduced or eliminated, thereby completing the present disclosure.

The present disclosure has been made in an effort to provide a transformed Synechococcus elongatus strain capable of mass production of farnesene.

Further, the present disclosure has been made in an effort to provide a method for mass production of farnesene, including culturing the Synechococcus elongatus strain of the present disclosure.

In order to achieve the objects of the present disclosure as described above, an exemplary embodiment of the present disclosure provides a Synechococcus elongatus strain including the farnesene synthase gene (AFS) consisting of the nucleotide sequence represented by SEQ ID NO: 4.

In another exemplary embodiment of the present disclosure, the strain further includes a deoxyxylulose-5-phosphate synthase gene (dxs) consisting of the nucleotide sequence represented by SEQ ID NO: 1.

In yet another exemplary embodiment of the present disclosure, the strain further includes an isopentenyl-diphosphate delta isomerase (idi) gene consisting of the nucleotide sequence represented by SEQ ID NO: 2 and a farnesyl diphosphate synthase (ispA) gene consisting of the nucleotide sequence represented by SEQ ID NO: 3.

In yet another exemplary embodiment of the present disclosure, the strain is a strain of Accession No. KCCM 12133P.

In yet another exemplary embodiment of the present disclosure, the strain is transformed with a pSe2Bb1k-AFS recombinant vector having the vector map of FIG. 5.

In yet another exemplary embodiment of the present disclosure, the strain is further transformed with a pSe1Bb1s-dxs recombinant vector having the vector map of FIG. 6.

In yet another exemplary embodiment of the present disclosure, the strain is further transformed with the pSe1Bb1s-dxs, idi, ispA recombinant vector having the vector map of FIG. 7.

In yet another exemplary embodiment of the present disclosure, the pSe2Bb1k-AFS recombination vector is inserted into the Neutral site-II of the wild-type Synechococcus elongatus strain.

In yet another exemplary embodiment of the present disclosure, the pSe1Bb1s-dxs recombination vector or the pSe1Bb1s-dxs, idi, ispA recombination vector is inserted into the Neutral site-I of the wild-type Synechococcus elongatus strain.

In yet another exemplary embodiment of the present disclosure, the strain produces farnesene using carbon dioxide.

Yet another exemplary embodiment of the present disclosure provides a method for the mass production of farnesene, including culturing the Synechococcus elongatus strain of the present disclosure.

In yet another exemplary embodiment of the present disclosure, culturing the strain includes supplying carbon dioxide.

In yet another exemplary embodiment of the present disclosure, the method further includes obtaining farnesene dissolved in a hydrophobic solvent.

Yet another exemplary embodiment of the present disclosure provides a method for eliminating or reducing carbon dioxide, including culturing the Synechococcus elongatus strain of the present disclosure.

According to the exemplary embodiments of the present disclosure, the transformed Synechococcus elongatus strain of the present disclosure is characterized by having the ability to mass produce farnesene using carbon dioxide as an independent carbon source. In particular, the Synechococcus elongatus strain is economically effective because it uses carbon dioxide present in light and air as a carbon source. There is an eco-friendly effect since it can be used for eliminating or reducing carbon dioxide in the atmosphere using microorganisms. Further, the strain of the present disclosure has a rapid growth rate and excellent ability to fix carbon dioxide compared with other microorganisms, thereby being utilized in various fields such as food, medicine, pharmacy, biofuel, and chemistry.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION OF THE INVENTION

Figure 1:
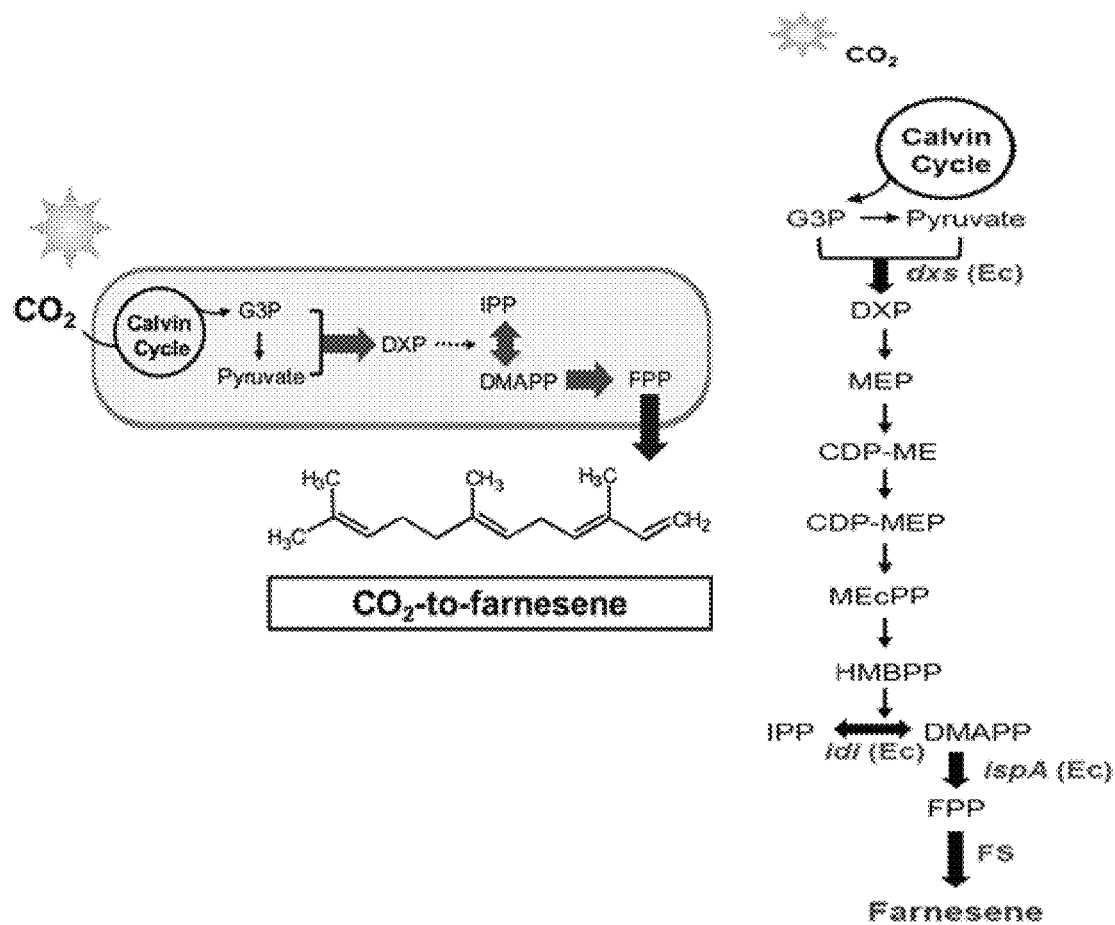
FIG. 1 schematically illustrates a farnesene production pathway of transformed Synechococcus elongatus strains according to the present disclosure.

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

The present disclosure is characterized by proving the transformed Synechococcus elongatus strains for which farnesene is mass-produced.

Synechococcus elongatus is a kind of cyanobacteria. Cyanobacterium, a prokaryotic cell, is easy to be genetically manipulated, which is advantageous in altering the metabolic pathway or artificially controlling metabolites. The present inventors produced transformed Synechococcus elongatus strains capable of mass production of farnesene using these characteristics of cyanobacteria and synthetic biology/metabolism engineering techniques.

In particular, the transformed Synechococcus elongatus strain provided in the present disclosure includes a farnesene synthase gene (AFS). The AFS gene is a gene encoding an enzyme that produces farnesene from a farnesyl diphosphate (FPP), which preferably has the nucleotide sequence represented by SEQ ID NO: 4.

Further, the transformed Synechococcus elongatus strains according to the present disclosure may further include a deoxyxylulose-5-phosphate synthase gene (dxs) in addition to the AFS gene.

The deoxyxylulose-5-phosphate synthase gene (dxs) is a gene encoding an enzyme that produces 1-deoxy-D-xylulose 5-phosphate (DXP) from pyruvate and D-glyceraldehyde 3-phosphate (G3P), which preferably has the nucleotide sequence represented by SEQ ID NO: 1.

Further, the transformed Synechococcus elongatus strains according to the present disclosure may further include an isopentenyl-diphosphate delta isomerase (idi) gene and a farnesyl diphosphate synthase (ispA) gene in addition to the deoxyxylulose-5-phosphate synthase gene (dxs) and deoxyxylulose-5-phosphate synthase gene (dxs).

The isopentenyl-diphosphate delta isomerase (idi) gene is a gene encoding an enzyme that produces dimethylallyl diphosphate (DMAPP) from isopentenyl-diphosphate, which preferably has the nucleotide sequence represented by SEQ ID NO: 2.

The farnesyl diphosphate synthase (ispA) gene is a gene encoding an enzyme that produces farnesyl diphosphate (FPP) from dimethylallyl diphosphate, which preferably has the nucleotide sequence represented by SEQ ID NO: 3.

Further, according to one embodiment of the present disclosure, the farnesene synthase gene (AFS) was used one derived from apple, and deoxyxylulose-5-phosphate synthase gene (dxs), isopentenyl-diphosphate delta isomerase (idi) gene, and farnesyl diphosphate synthase (ispA) gene were used ones derived from *Escherichia coli*.

Further, the Synechococcus elongatus strain according to the present disclosure, which is capable of mass-producing farnesene is a recombinant vector including the farnesene synthase gene (AFS), the deoxyxylulose-5-phosphate synthase gene (dxs), isopentenyl-diphosphate delta isomerase (idi) gene or farnesyl diphosphate synthase (ispA) gene, which can be produced by transforming the wild-type Synechococcus elongatus strain (parent strain).

Each of the genes contained in the recombinant vector is transfected into the parent strain, and thus it is codon-optimized for stable expression.

The term "codon-optimized" means that the target nucleic acid sequence is properly expressed in the host cell transformed with the target base sequence (nucleic acid sequence) and the target nucleic acid sequence reflects the codon usage of the selected host cell for the further expression in high level. For example, the nucleotide sequence of the AFS, dxs, idi, or ispA of the present disclosure can be regulated to match the codon usage of Synechococcus elongatus. The term "codon-usage" means a nucleic acid sequence frequently used to encode each amino acid according to an organism. A table of codon usage for a number of organisms is available, which can be used as a reference for designing the sequence of the present disclosure (See Gouy and Gautier (1982) Nucleic Acids Res 10 (22) 7055-7074; Eyre-Walker (1996) Mol. Biol Evol 13 (6) 864-872). When the most frequently used codon among the codons of a given host microorganism is used, the possibility of the translation is generally increased to enhance the expression level of the desired sequence.

The term "recombinant vector" used herein refers to a vector which can express a target protein or target RNA in a suitable host cell, which means a gene construct containing an essential regulatory element operably linked so as to express a gene insert. The term "operably linked" used herein refers to a functional linkage between a nucleic acid expression regulatory sequence and a nucleic acid sequence encoding a target protein or RNA so as to perform a general function. For example, a promoter and a nucleic acid sequence encoding a protein or RNA are operably linked so as to affect the expression of a nucleic acid sequence for encoding. Operable linkage with a recombinant vector can be performed using gene recombination techniques well known in the art. Site-specific DNA cleavage and linkage are performed using enzymes generally known in the art.

Further, the vectors used for transformation in the present disclosure include, but are not limited to, plasmid vectors, cosmid vectors, bacteriophage vectors, and viral vectors. Suitable expression vectors may include an expression regulatory element such as a promoter, an operator, an initiation codon, a stop codon, a polyadenylation signal, or an enhancer, as well as a signal sequence or a reader sequence for membrane targeting and secretion, and may be variously manufactured so as to be adapted for some purposes. The promoter of the vector may be constructive or inductive. Furthermore, the expression vector includes a selective marker for selecting a host cell containing the vector, and a replicable expression vector includes a replication origin.

Figure 5:
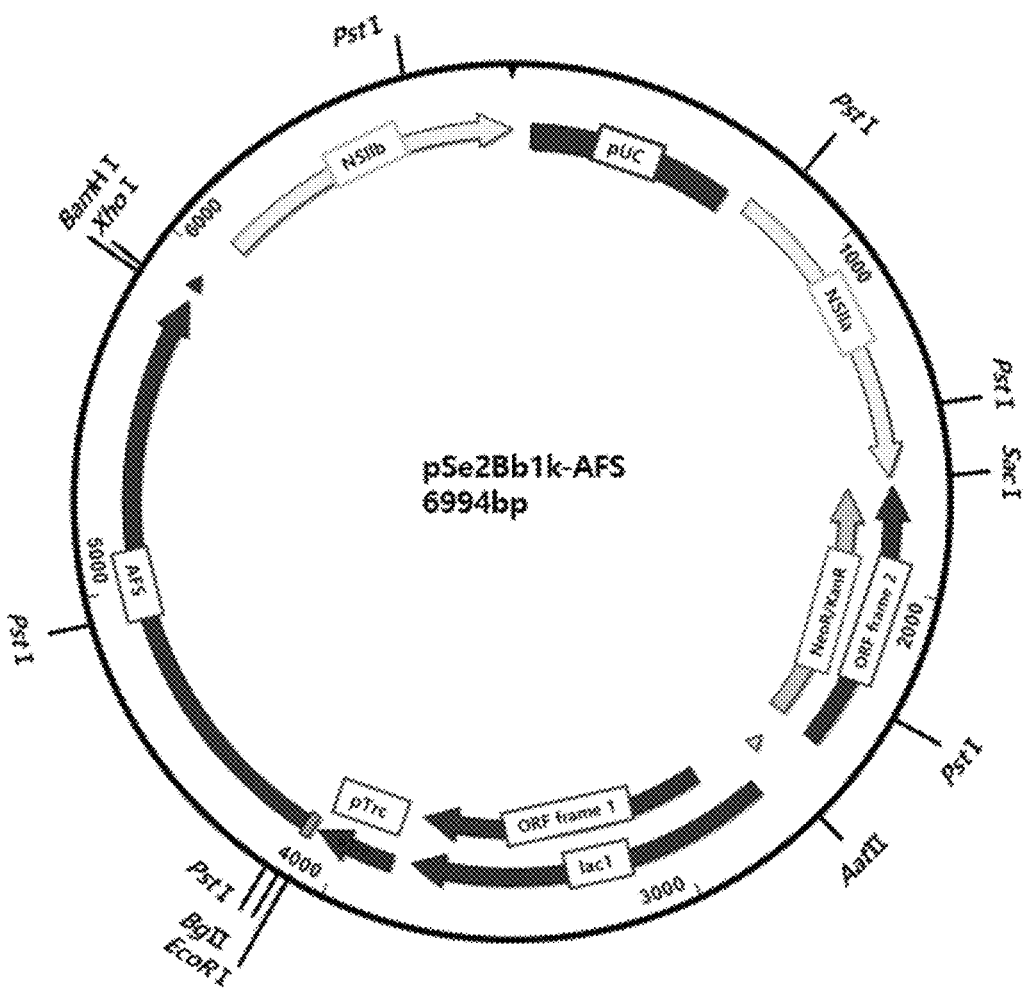
FIG. 5 illustrates the pSe2Bb1k-AFS recombination vector structure of the present disclosure.
Figure 6:
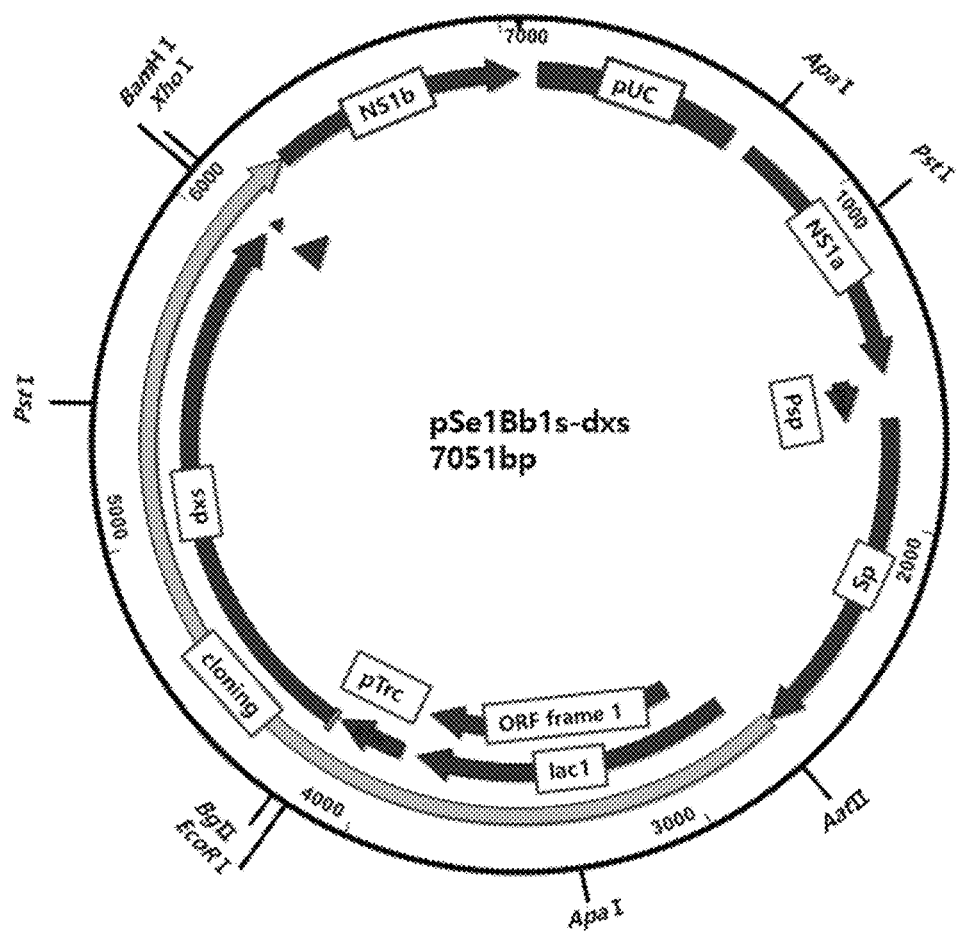
FIG. 6 illustrates the pSe1Bb1s-dxs recombination vector structure of the present disclosure.
Figure 7:
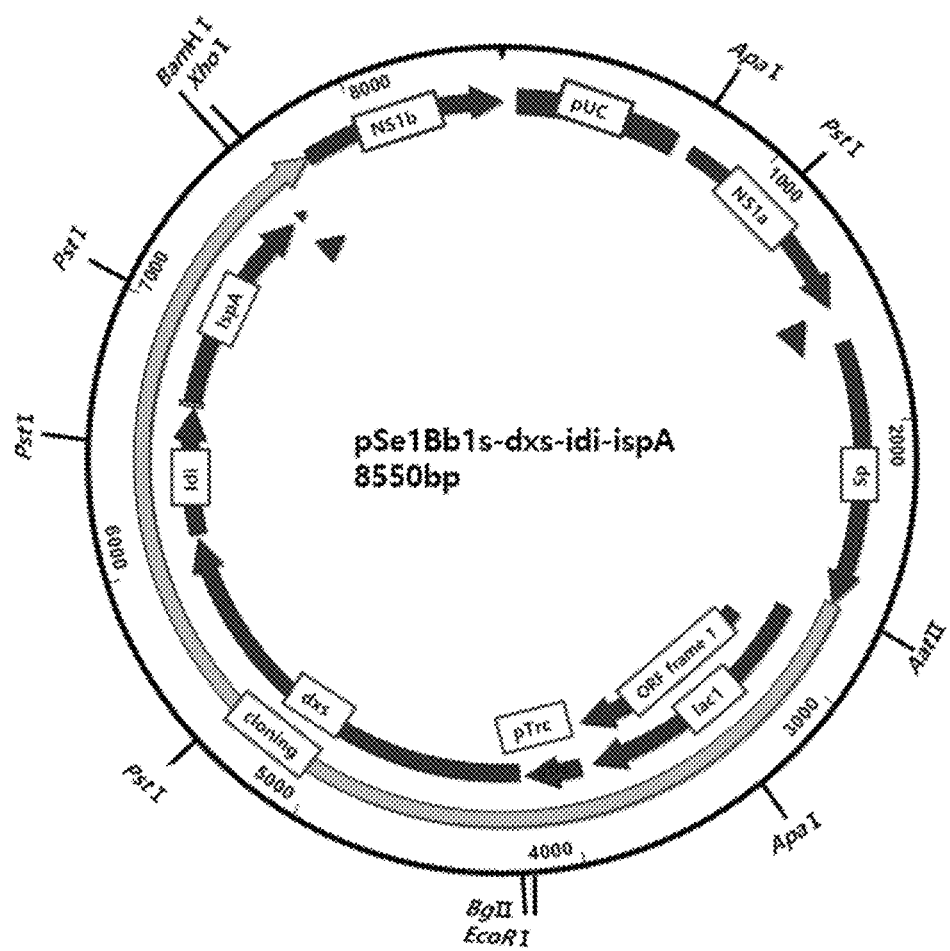
FIG. 7 illustrates the pSe1Bb1s-dxs, idi, ispA recombination vector structure of the present disclosure.

In one embodiment of the present disclosure, in order to prepare transformed Synechococcus elongatus strains, Synechococcus elongatus was transformed using one or more vectors selected from the group consisting of a pSe2Bb1k-AFS recombinant vector having the vector map of FIG. 5, a pSe1Bb1s-dxs recombinant vector having the vector map of FIG. 6, and pSe1Bb1s-dxs, idi, and ispA recombinant vector having the vector map of FIG. 7.

The transformation according to the present disclosure includes any method of introducing the desired gene (nucleic acid) into an organism, cell, tissue or organ. As known in the art, a suitable standard technique may be selected depending on the host cell to perform the transformation. Such methods include, but is not limited to, electroporation, protoplast fusion, calcium phosphate ($CaPO_4$) precipitation, calcium chloride ($CaCl_2$) precipitation, stirring with silicon carbide fibers, Agrobacterium-mediated transformation, PEG, dextran sulfate, Lipofectamine, heat shock method, and the like.

In one embodiment of the present disclosure, the wild-type Synechococcus elongatus PCC 7942 strain is used as a parent strain for transformation, and the recombinant vector as described above ws used to prepare transformed Synechococcus elongatus strains capable of mass-producing farnesene.

Further, in one embodiment of the present disclosure, the pSe2Bb1k-AFS recombinant vector is inserted into the Neutral site-II of the wild-type Synechococcus elongatus strain, and the pSe1Bb1s-dxs recombinant vector or pSe1Bb1s-dxs, idi, ispA recombinant vector is inserted into the Neutral site-I of the wild-type Synechococcus elongatus strain.

The Synechococcus elongatus strain according to the present disclosure, which is transformed in the same manner, is characterized by mass-producing farnesene using carbon dioxide.

Figure 4:
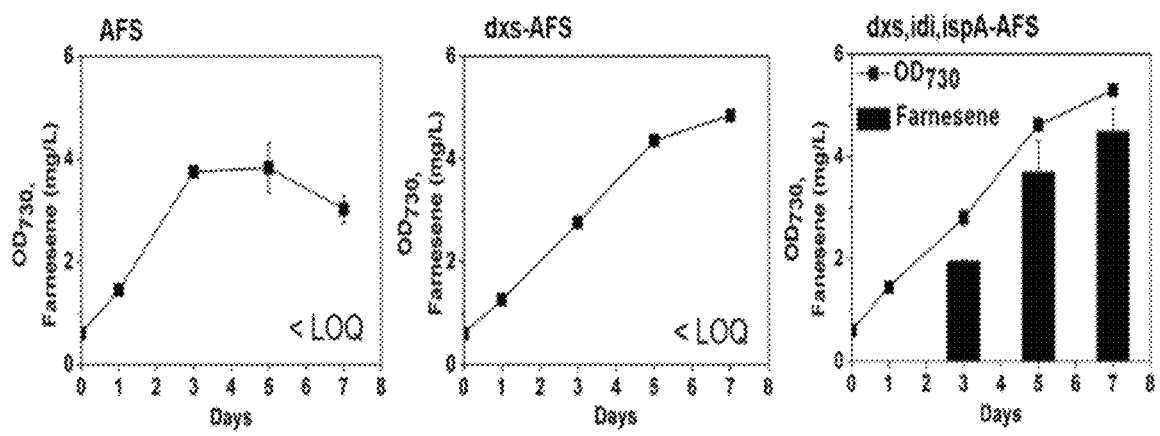
FIG. 4 illustrates the results of measuring the amount of farnesene produced from transformed Synechococcus elongatus strains of the present disclosure.

In order to confirm this characteristic, the present inventors cultured transformed Synechococcus elongatus strains according to the present disclosure under the conditions of supplying carbon dioxide, then obtained farnesene, and analyzed the yields. The results indicate that the transformed Synechococcus elongatus strain into which all the dxs gene, idi gene, ispA gene, and AFS gene are inserted shows maximum 4.6 mg/L of the production of farnesene (See FIG. 4). Such yield is significantly increased compared to the prior art.

Thus, the present disclosure provides a method for the mass-production of farnesene, including culturing the transformed Synechococcus elongatus strain according to the present disclosure. Culturing the strain may include supplying carbon dioxide.

Also, the method may further include isolating and obtaining farnesene dissolved in the hydrophobic solvent. The hydrophobic solvent may be used without limitation as long as they are known in the art. Farnesene produced by the strain may be accumulated in the hydrophobic solvent. The Synechococcus elongatus strain of the present disclosure secretes the produced farnesene extracellularly, and the secreted farnesene is dissolved in the hydrophobic solvent.

Further, the present disclosure provides a method of eliminating or reducing carbon dioxide, including culturing the transformed Synechococcus elongatus strain according to the present disclosure.

The strain according to the present disclosure may utilize carbon dioxide present in light and air as a carbon source, thereby effectively eliminating or reducing carbon dioxide in the atmosphere.

Hereinafter, the present disclosure is described in more detail in company with Examples. These Examples are intended to more particularly illustrate the present disclosure, and the scope of the present disclosure is not limited to these embodiments.

Example 1

Strategy for the Mass Production of Farnesene from Synechococcus elongatus Strain A novel metabolic pathway to farnesene was constructed using the dxs, idi, and ispA genes which were used in the optimized MEP metabolic pathway with reference to the prior art documents, which is illustrated as a schematic diagram in FIG. 1 (Choi S Y, Lee H J, Choi J, Kim J, Sim S J, Um Y, Kim Y, Lee T S, Keasling J, Woo H M (2016) Photosynthetic conversion of CO2 to farnesyl diphosphate-derived phytochemicals (amorpha-4,11-diene and squalene) by engineered cyanobacteria. Biotechnol Biofuels 69:202). DNA sequence of farnesene synthase (AFS) gene of apple (Malus×domestica) was codon-optimized, and sequences were synthesized and manufactured in Genscript®. Thus, the sequences were used in the following Examples. Pyruvate and dxs, an enzyme gene that produces 1-deoxy-D-xylulose 5-phosphate (DXP) from D-glyceraldehyde 3-phosphate (G3P), idi, an enzyme gene that produces dimethylallyl diphosphate (DMAPP) from isopentenyl diphosphate (IPP) and ispA, an enzyme gene that produces farnesyl diphosphate (FPP) from dimethylallyl diphosphate (DMAPP) were derived from *Escherichia coli*.

Example 2

Preparation of Recombinant Vector for Mass Production of Farnesene

The present inventors first produced the recombinant vectors as described below for the preparation of transformed Synechococcus elongatus strains capable of mass-producing farnesene.

① Production of pSe1Bb1s-Dxs Vector

The gfp portion of pSe1Bb1s-gfp, SyneBrick vector, (Kim U J, Lee S M, Um Y, Sim S J, Woo H M (2017) Development of SyneBrick vectors as a synthetic biology platform for gene expression in Synechococcus elongatus PCC 7942. Front Plant Sci 8: 293) was removed using EcoRI-BamHI restriction enzyme, and then the DNA sequence (SEQ ID NO: 1) of the deoxyxylulose-5-phosphate synthase gene (dxs) was inserted into the site to prepare a pSe1Bb1s-dxs recombinant vector, which is illustrated in FIG. 6. The recombinant vector was produced into which the dxs gene encoding an enzyme which produces 1-deoxy-D-xylulose 5-phosphatase (DXP) from pyruvate and D-glyceraldehyde 3-phosphate (G3P) was inserted.

② Production of pSe1Bb1s-Dxs, Idi, ispA Vectors

The gfp portion of the pSe1Bb1s-gfp vector, which is the same SyneBrick vector used in Example as described above, was removed using EcoRI-BamHI restriction enzyme, and the DNA sequence of dxs, idi (SEQ ID NO: 2) and ispA (SEQ ID NO: 3) genes were sequentially inserted into the site to produce PSe1Bb1s-dxs, idi, and ispA recombinant vectors (See FIG. 7).

In this Example, the dxs gene is the same as that of Example 1 as described above. The idi gene is a gene encoding an enzyme that produces dimethylallyl diphosphate (DMAPP) from isopentenyl diphosphate (IPP). The ispA gene is a gene encoding an enzyme that produces farnesyl diphosphate (FPP) from dimethylallyl diphosphate.

③ Production of pSe2Bb1k-AFS Vector

Further, the present inventors removed gfp portion of pSe2Bb1k-gfp vector (Chwa J W, Kim U J, Sim S J, Um Y, Woo H M (2016) Engineering of a modular and synthetic phosphoketolase pathway for photosynthetic production of acetone from CO2 in Synechococcus elongatus PCC 7942 under light and aerobic condition. Plant Biotech J 14:1768-1776) using the EcoRI-BamHI restriction enzyme. Then, the DNA sequence (SEQ ID NO: 4) of the farnesene synthase gene (AFS) was inserted into the site to prepare a pSe2Bb1k-AFS recombinant vector (See FIG. 5). In this Example, the AFS gene is a gene encoding an enzyme that produces farnesene from farnesyl diphosphate (FPP).

Example 3

Production of Synechococcus elongatus Strain with the Ability to Mass-Produce Farnesene Transformed with the Recombinant Vector of the Present Disclosure Transformed Synechococcus elongatus strains to have the ability to mass-produce farnesene with the MEP metabolic pathway were prepared by transforming the wild-type Synechococcus elongatus PCC 7942 strain with the three recombinant vectors prepared in Example 2 as described above. Such a scheme is described in detail as follows.

Figure 2:
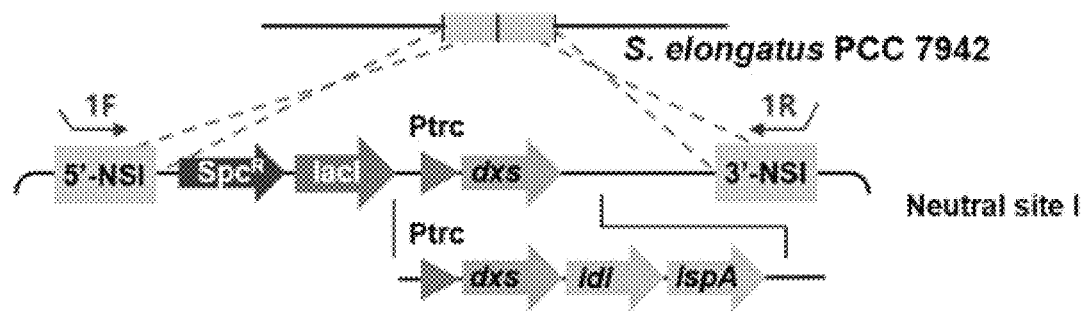
FIG. 2 is a schematic diagram of a recombinant vector used for preparing transformed Synechococcus elongatus strains having the farnesene-producing ability of the present disclosure.
Figure 2:
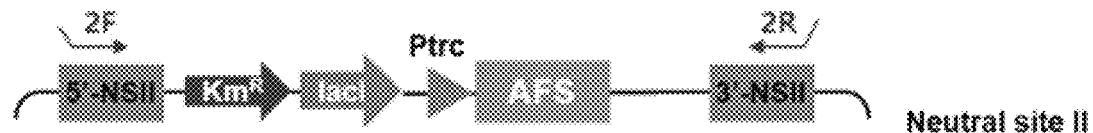

First, the pSe2Bb1k-AFS vector prepared in Example 2 was inserted into Neutral site-II of wild-type Synechococcus elongatus PCC 7942 strain to prepare a strain for producing farnesene. Then, pSe1Bb1s-dxs vector, and pSe1Bb1s-dxs, idi and ispA vectors, respectively were introduced into the pSe2Bb1k-AFS vector-introduced strain to prepare Synechococcus elongatus strains (See FIG. 2).

Here, pSe1Bb1s-dxs vector and pSe1Bb1s-dxs, idi, ispA vectors, respectively, were inserted into Neutral site-I of wild-type Synechococcus elongatus PCC 7942 strain.

The transformation was performed using the Natural transformation method.

Further, the present inventors deposited the Synechococcus elongatus strain in which pSe2Bb1k-AFS vector-introduced strain was transformed with the pSe1Bb1s-dxs, idi, and ispA vectors in Korean Culture Center of Microorganisms on Oct. 18, 2017. Accession number: KCCM12133P was received from the Korean Culture Center of Microorganisms.

In order to check whether or not strains were adequately transformed with the recombinant vector produced in the present disclosure, a PCR method was performed using a primer as described below. The results show that the transformation was carried out using the recombinant vectors of the present disclosure. Whether or not to be transformed can be confirmed by PCR product sizes using the following primers. Sequencing analysis using PCR products confirmed that the vectors were inserted well into the Synechococcus elongatus chromosome.

```
<Primer sequence>
                                       (SEQ ID NO: 5)
NSI-forward:    AAG CGC TCC GCA TGG ATC TG (SEQ ID NO: 6)
NSI-reverse:    CAA GGC AGC TTG GAA GGG CG (SEQ ID NO: 7)
NSII-forward:   GGC TAC GGT TCG TAA TGC CA (SEQ ID NO: 8)
NSII-reverse:   GAG ATC AGG GCT GTA CTT AC
```

Example 4

Confirmation of Farnesene Production Ability of Transformed Synechococcus elongatus Strains of the Present Disclosure Using Carbon Dioxide Three kinds of transformed strains of the present disclosure prepared in Example 3 as described above were cultured in order to analyze whether farnesene can be directly produced from 5% carbon dioxide. For such purpose, 80 mL BG-11 medium containing 10 mM MOPS buffer was added to a 100 mL culture container. Each of three farnesene-producing transformed strains of the present disclosure prepared in Example as described above was diluted to OD 0.6 at the initial stage of the culture and then was added thereto. During the culture, 10 μg/ml spectinomycin antibiotics and 10 μg/ml kanamycin antibiotics were added thereto and cultured in an incubator under the conditions of continuously supplying 100 μE·m−2·s−1 5% CO2 at 30° C. After culturing for 24 hours, 1 mM IPTG, an inducer necessary for gene expression, and 20% dodecane, which inhibits cell toxicity from farnesene produced were treated. After 7 days of culture, an optical density at a wavelength of 740 nm and an amount of farnesene production of dodecane layer were measured. Here, the three kinds of mutant strains refer to (i) Synechococcus elongatus strains into which only pSe2Bb1k-AFS vector was introduced, (ii) Synechococcus elongatus strains in which pSe1Bb1s-dxs vector was introduced into the pSe2Bb1k-AFS-introduced strain and (iii)

Synechococcus elongatus strains in which pSe1Bb1s-dxs, idi, ispA vectors were introduced into the pSe2Bb1k-AFS-introduced strain.

Then, in order to check whether the transformed strains of the present disclosure produced farnesene, 900 μL ethyl acetate (including 5 μg/mL caryophyllene as an internal standard) was added to 100 μl the dodecane layer, and then GC-MS analysis was performed.

Figure 3:
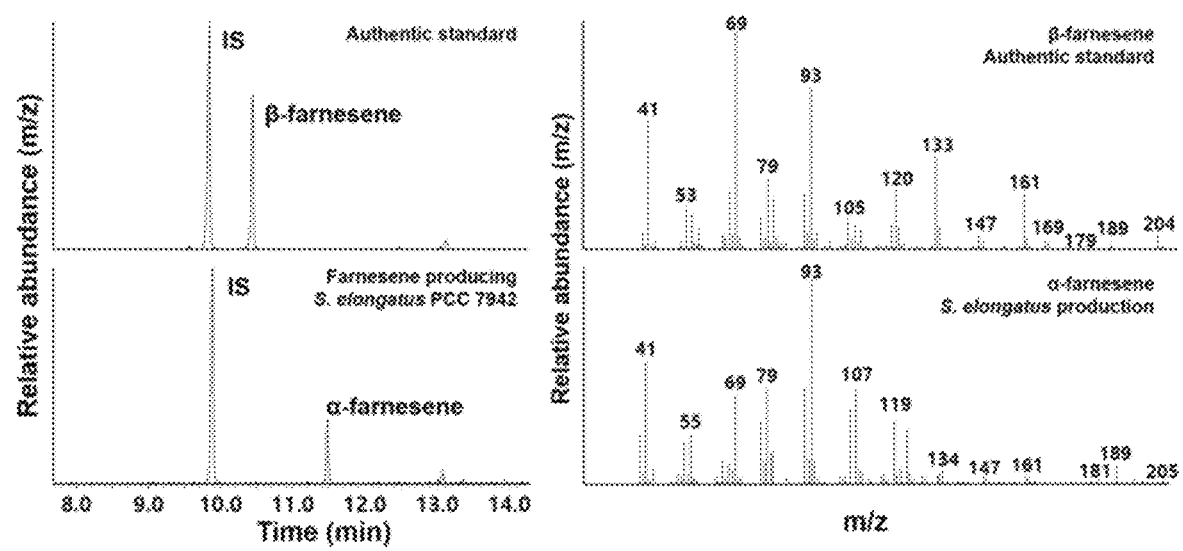
FIG. 3 illustrates the results of confirming, by GC/MS analysis, whether to prepare farnesene from transformed Synechococcus elongatus strains of the present disclosure.

As illustrated in FIG. 3, the results demonstrate that the peak of the substance produced by the strains of the present disclosure exactly matches that of the beta-farnesene (No. 73492, Sigma-Aldrich) used as a control, indicating that the substance produced from the strains of the present disclosure is farnesene (alpha-farnesene).

Thus, these results show that the transformed Synechococcus elongatus strains produced in the present disclosure can produce farnesene from carbon dioxide.

Further, it was confirmed that all of the three transgenic strains prepared in the present disclosure could produce farnesene from carbon dioxide. In particular, the transformed Synechococcus elongatus strain into which the dxs gene, idi gene, ispA gene, and AFS gene were inserted produces farnesene in maximum 4.6 mg/L, indicating that it has a very high ability to produce farnesene (See FIG. 4).

As described above, the present disclosure is described with reference to the preferred Examples. It should be understood by those of ordinary skill in the art to which the present disclosure belongs that the present disclosure may be embodied in a modified form without departing from the essential characteristics of the present disclosure. Therefore, it should be considered that Examples are described for illustrative purpose rather than restrictive purpose. The scope of the present disclosure is set forth in the appended claims rather than the foregoing description. All differences within the scope of equivalents thereof should be construed as being included in the present disclosure.

From the foregoing, it will be appreciated that various embodiments of the present disclosure have been described herein for purposes of illustration and that various modifications may be made without departing from the scope and spirit of the present disclosure. Accordingly, the various embodiments disclosed herein are not intended to be limiting, with the true scope and spirit being indicated by the following claims.

ACCESSION NUMBER

Depositary Institution: Korean Culture Center of Microorganisms (overseas)
Accession number: KCCM12133P
Commissioned date: Oct. 18, 2017

What is claimed is:

1. A Synechococcus elongatus strain comprising a farnesene synthase gene (FS) consisting of the nucleotide sequence of SEQ ID NO: 4.

2. The Synechococcus elongatus strain according to claim 1, the strain further comprising a deoxyxylulose-5-phosphate synthase gene (dxs) consisting of the nucleotide sequence of SEQ ID NO: 1.

3. The Synechococcus elongatus strain according to claim 2, the strain further comprising an isopentenyl-diphosphate delta isomerase (idi) gene consisting of the nucleotide sequence of SEQ ID NO: 2 and a farnesyl diphosphate synthase (ispA) gene consisting of the nucleotide sequence of SEQ ID NO: 3.

4. The Synechococcus elongatus strain according to claim 3, wherein the strain is a strain of Accession No. KCCM 12133P.

5. The Synechococcus elongatus strain according to claim 1, wherein the strain is transformed with a pSe2Bb1k-AFS recombinant vector having the vector map of FIG. 5.

6. The Synechococcus elongatus strain according to claim 2, wherein the strain is further transformed with a pSe1 Bb1 s-dxs recombinant vector having the vector map of FIG. 6.

7. The Synechococcus elongatus strain according to claim 3, wherein the strain is further transformed with a pSe1 Bb1 s-dxs, idi, ispA recombinant vector having the vector map of FIG. 7.

8. The Synechococcus elongatus strain according to claim 5, wherein the pSe2Bb1k-AFS recombination vector is inserted into a Neutral site-II of a wild-type Synechococcus elongatus strain.

9. The Synechococcus elongatus strain according to claim 6, wherein the pSe1Bb1s-dxs recombination vector is inserted into a Neutral site-I of a wild-type Synechococcus elongatus strain.

10. The Synechococcus elongatus strain according to claim 1, wherein the strain produces farnesene using carbon dioxide.

11. A method for a mass production of a farnesene, comprising culturing the strain according to claim 1.

12. The method according to claim 11, wherein culturing the strain includes supplying carbon dioxide.

13. The method according to claim 11, the method further comprising obtaining the farnesene dissolved in a hydrophobic solvent.

14. A method for eliminating or reducing carbon dioxide, comprising culturing the strain according to claim 1.

15. The Synechococcus elongatus strain according to claim 7, wherein the pSe1 Bb1 s-dxs, idi, ispA recombination vector is inserted into a Neutral site-I of a wild-type Synechococcus elongatus strain.

* * * * *